(12) United States Patent
Hamada et al.

(10) Patent No.: US 6,718,005 B2
(45) Date of Patent: Apr. 6, 2004

(54) NONCONTACT TYPE SIGNAL TRANSMISSION DEVICE AND X-RAY COMPUTED TOMOGRAPHY APPARATUS INCLUDING THE SAME

(75) Inventors: Yuji Hamada, Otawara (JP); Kyojiro Nambu, Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/559,071

(22) Filed: Apr. 27, 2000

(65) Prior Publication Data

US 2003/0156678 A1 Aug. 21, 2003

(30) Foreign Application Priority Data

Apr. 28, 1999 (JP) ............................................ 11-122886

(51) Int. Cl.[7] .................................................. G21K 1/12
(52) U.S. Cl. ........................................ 378/15; 250/551
(58) Field of Search .............................. 378/15, 4, 19, 378/20, 84, 85; 250/551, 217, 208.1

(56) References Cited

U.S. PATENT DOCUMENTS

| | | | | |
|---|---|---|---|---|
| 4,259,584 A | * | 3/1981 | Krumme | 250/445 T |
| 4,996,435 A | * | 2/1991 | Keller | 250/551 |
| 5,134,639 A | * | 7/1992 | Vekstein et al. | 378/15 |
| 5,336,897 A | * | 8/1994 | Watanabe et al. | 250/551 |
| 5,354,993 A | * | 10/1994 | Kedmi et al. | 250/551 |

FOREIGN PATENT DOCUMENTS

| | | | |
|---|---|---|---|
| JP | 5-274587 | * | 10/1993 |
| JP | 7-079963 | | 3/1995 |

* cited by examiner

*Primary Examiner*—Craig E Church
*Assistant Examiner*—Irakli Kiknadze
(74) *Attorney, Agent, or Firm*—Oblon, Spivak, McClelland, Maier & Neustadt, P.C.

(57) ABSTRACT

A noncontact type signal transmission device performs noncontact transmission of signals between a first member and a second member by using light. The second member moves along a predetermined orbit relative to the first member. A plurality of light-emitting devices are arranged on one of the first and second members. A plurality of light-receiving devices are arranged on the other of the first and second members. Light emitted from the light-emitting devices is received by the light-receiving devices. Beam condensing devices are disposed between the light-emitting devices and the light-receiving devices. Each beam condensing device has a function of condensing light from the light-emitting device in a direction substantially perpendicular to the orbit. The function of each beam condensing device is to increase the amount of light received by each light-receiving device and to improve light reception sensitivity.

1 Claim, 8 Drawing Sheets

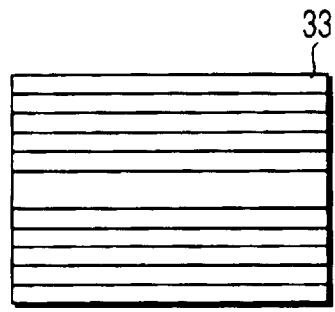
FIG. 14A      FIG. 14B
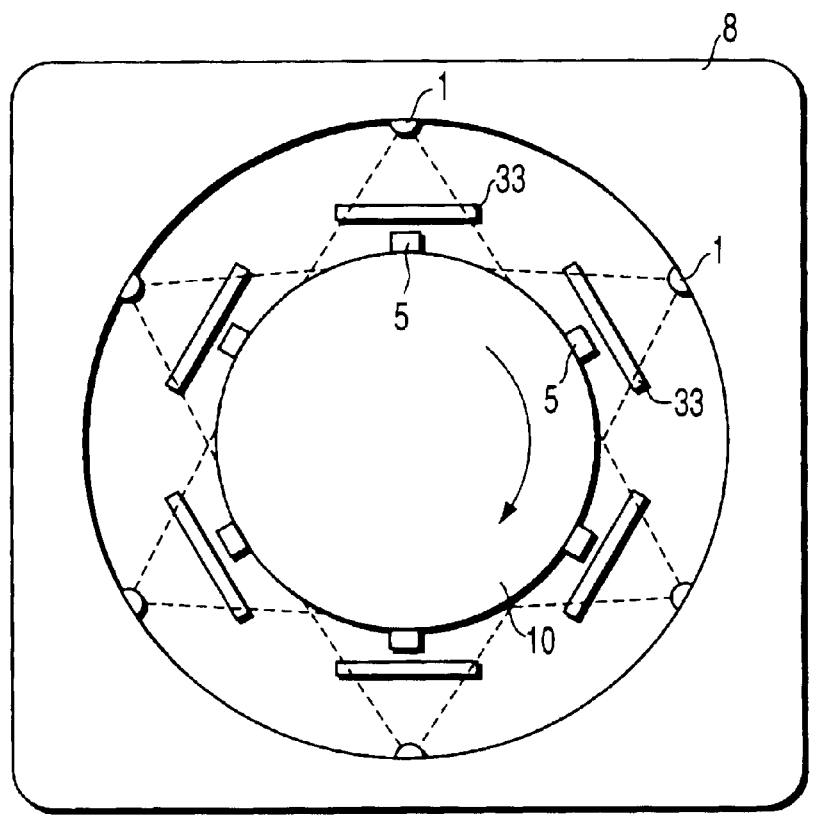
FIG. 15

NONCONTACT TYPE SIGNAL TRANSMISSION DEVICE AND X-RAY COMPUTED TOMOGRAPHY APPARATUS INCLUDING THE SAME

CROSS-REFERENCE TO RELATED APPLICATIONS

This application is based upon and claims the benefit of priority from the prior Japanese Patent Application No. 11-122886, filed Apr., 28, 1999, the entire contents of which are incorporated herein by reference.

BACKGROUND OF THE INVENTION

The present invention relates to a noncontact type signal transmission device which uses light to perform noncontact signal transmission between members whose relative positions change.

A noncontact type signal transmission device of this type is used, for example, in an X-ray computed tomography apparatus. A noncontact type signal transmission device called a slip ring made up of an annular conductive ring and a conductive brush that comes into contact with the ring is used in many conventional X-ray computed tomography apparatuses to perform continuous rotation (continuous scanning). This slip ring makes much noise and hence is not suitable for weak signals, although it is suitable for the supply of power to an X-ray tube.

Recently, X-ray computed tomography apparatuses using noncontact type signal transmission devices have become available on the market.

As shown in FIG. 1, for example, a noncontact type signal transmission device used in an X-ray computed tomography apparatus is comprised of a stationary portion 301, a rotating ring 302 located inside the stationary portion 301, a plurality of light-emitting diodes 101 discretely arranged on the outer surface of the rotating ring 302, and a plurality of photodiodes 201 discretely arranged on the inner surface of the stationary portion 301. An analog signal output from an X-ray detector is coded into a binary code, and the light-emitting diodes 101 are turned on/off in accordance with the code. This turn on/off operation is decoded through the photodiodes 201.

For the sake of descriptive convenience, a rotating coordinate system X'Y'Z' is defined, which rotates about the rotation axis of the rotating ring 302 at an angular velocity equal to the rotational movement of the rotating ring 302. Assume that the X'-axis of this rotating coordinate system is the optical axis of light from the light-emitting diode 101 of interest, the Y'-axis is a tangent on the rotational orbit of the light-emitting diode 101 of interest, and the Z'-axis is an axis that is parallel to the rotation axis (orthogonal axis to the paper) and crosses the other axes at the light-emitting diode 101 of interest.

One of important parameters for the design of a noncontact type signal transmission device is the distance between each light-emitting diode 101 and a corresponding photodiode 201. As shown in FIG. 2, each photodiode 201 must be spaced apart from a corresponding light-emitting diode 101 by a certain distance so that the irradiation area from a given light-emitting diode 101 to the stationary portion 301 is seamlessly connected to (in practice, overlaps) the irradiation area from an adjacent light-emitting diode 101 to the stationary portion 301. If, however, each photodiode 201 is spaced apart from a corresponding light-emitting diode 101 too much, the amount of light received by the photodiode 201 decreases, resulting in a deterioration in sensitivity. The distance between each light-emitting diode 101 and a corresponding photodiode 201 must therefore be optimized.

In recent years, in the field of X-ray computed tomography apparatuses, techniques such as volume CT and digital rotational angiography have been put into practice. In some case, however, the amount of data handled in volume TC or the like becomes several ten or hundred times lager than the amount of data handled in single slice scanning.

To transmit such an enormous amount of data at high speed, the ON/OFF frequency of each light-emitting diode 101 must be increased to several MHz or several GHz in some cases.

If, however, the ON/OFF frequency of each light-emitting diode is increased, the amount of light emitted from the light-emitting diode decreases. Accordingly, the amount of light received by the photodiode decreases. As a consequence, a transmission error is likely to occur.

In general, the amount of light received is inversely proportional to the square of the distance between a light-emitting means and a light-receiving means. More specifically, as shown in FIG. 2, the amount of light received by the photodiode 201 decreases in inverse proportion to the square of a distance t1 between the light-emitting diode 101 and the photodiode 201. In contrast to this, the amount of light received increases as the distance t1 decreases. That is, a decrease in the amount of light received can be suppressed by brining the photodiode 201 close to the light-emitting diode 101.

If, however, each photodiode 201 is brought near a corresponding light-emitting diode 101 too much, an area appears, as shown in FIG. 3, in which the irradiation area from a given light-emitting diode 101 does not overlap that from the adjacent light-emitting diode 101. When the photodiode 201 passes through this non-overlap region, a transmission error tends to occur. However, if setting density of LED 101 is higher to eliminate the non-overlap region, a new problem of cost-up generates.

BRIEF SUMMARY OF THE INVENTION

It is an object of the present invention to provide a noncontact type signal transmission device which can transmit a large amount of data at high speed with high reliability.

A noncontact type signal transmission device includes light-emitting devices and light-receiving devices. The member mounting the light-emitting devices or the light-receiving devices moves along a predetermined orbit relative to the member mounting another. Beam condensing devices are disposed between the light-emitting devices and the light-receiving devices. Each beam condensing device has a function of condensing light from the light-emitting device in a direction substantially perpendicular to the orbit. The function of each beam condensing device is to increase the amount of light received by each light-receiving device and to improve light reception sensitivity.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 14A is a sectional view of a beam condensing device in FIG. 13;

FIG. 14B is a plan view of the beam condensing device in FIG. 13;

FIG. 15 is a view showing the structure of a noncontact type signal transmission device according to a modification of the second embodiment;

DETAILED DESCRIPTION OF THE INVENTION

The embodiments of the present invention will be described below with reference to the views of the accompanying drawing.

First Embodiment

Figure 1:
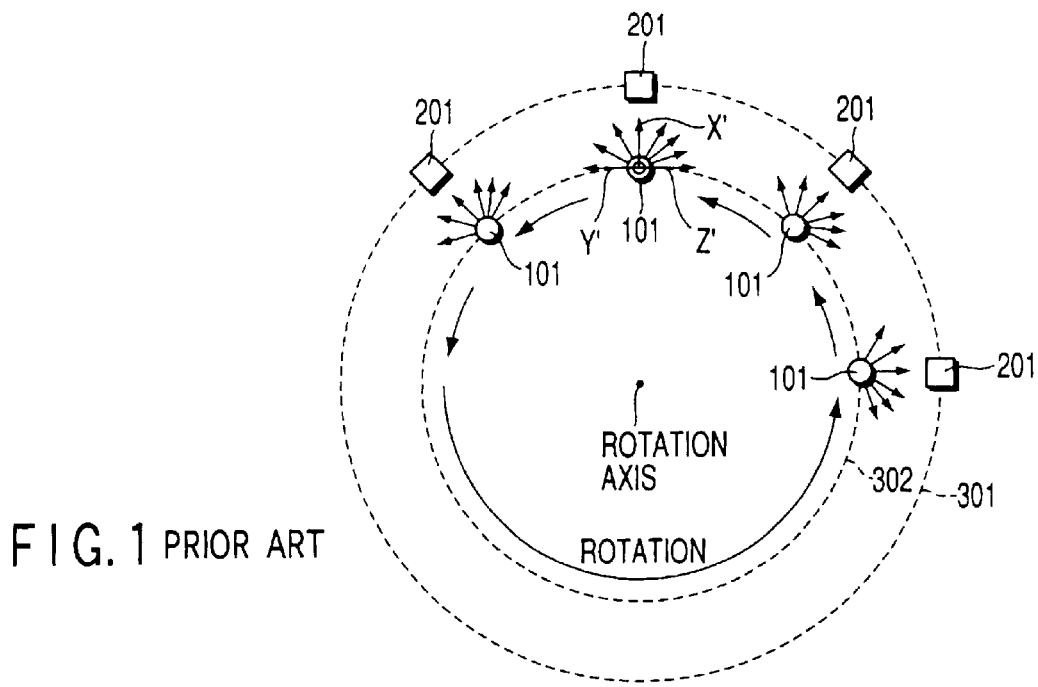
FIG. 1 is a schematic view showing a noncontact type signal transmission device mounted on the gantry of a conventional X-ray computed tomography apparatus.
Figure 2:
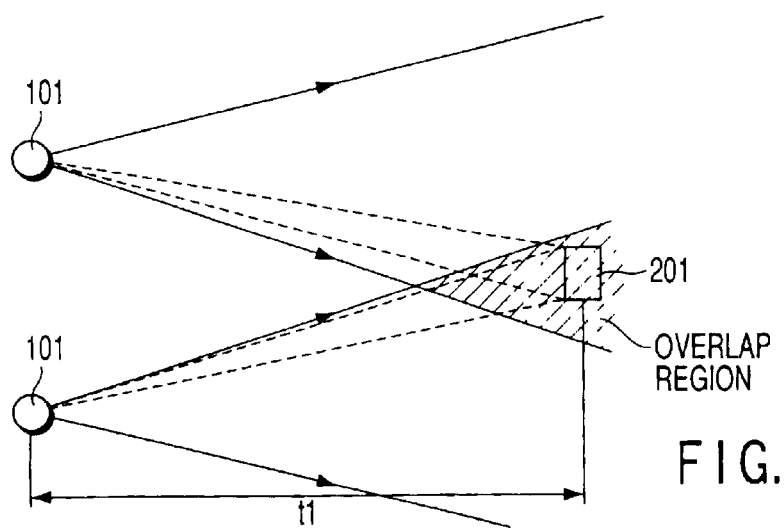
FIG. 2 is a view showing the position of a photodiode with respect to light-emitting diodes.
Figure 3:
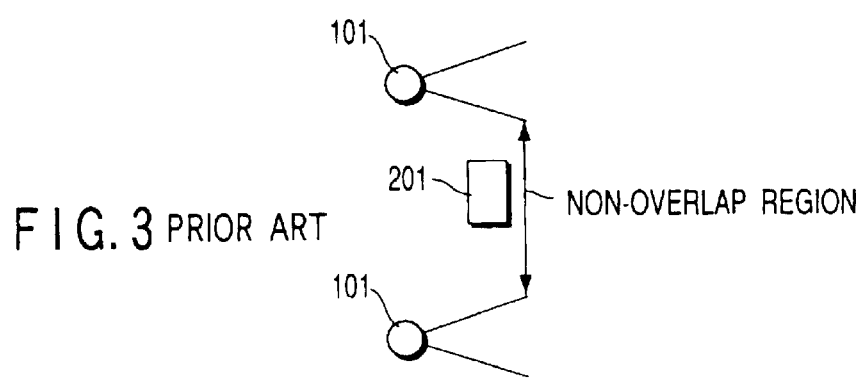
FIG. 3 is a view showing how a transmission error occurs when the photodiode is too close to the light-emitting diodes in FIG. 1.
Figure 4:
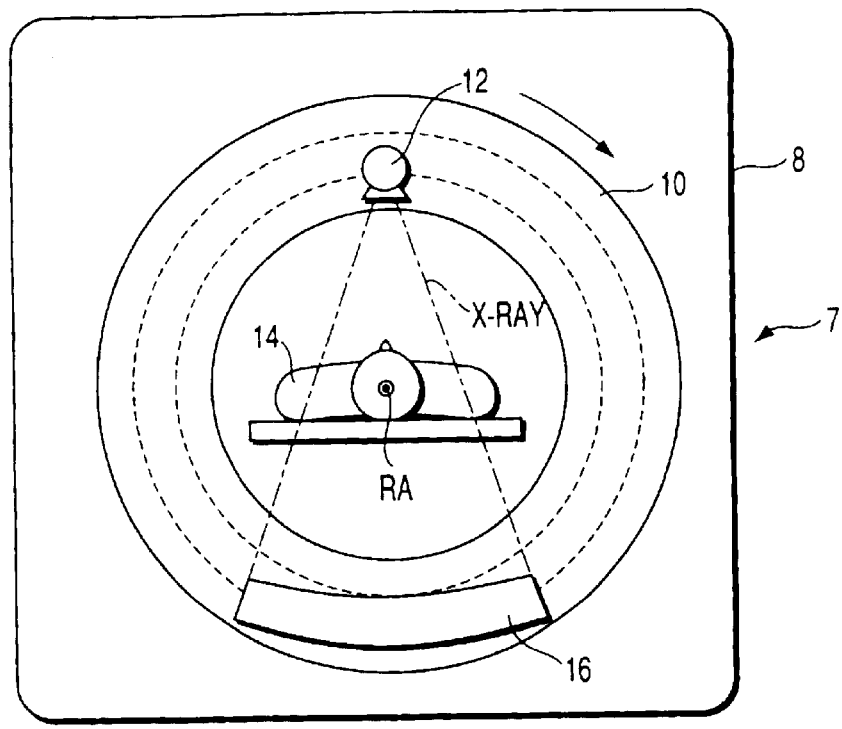
FIG. 4 is a view showing a noncontact type signal transmission device mounted in an X-ray computed tomography apparatus according to the first embodiment of the present invention.
Figure 5:
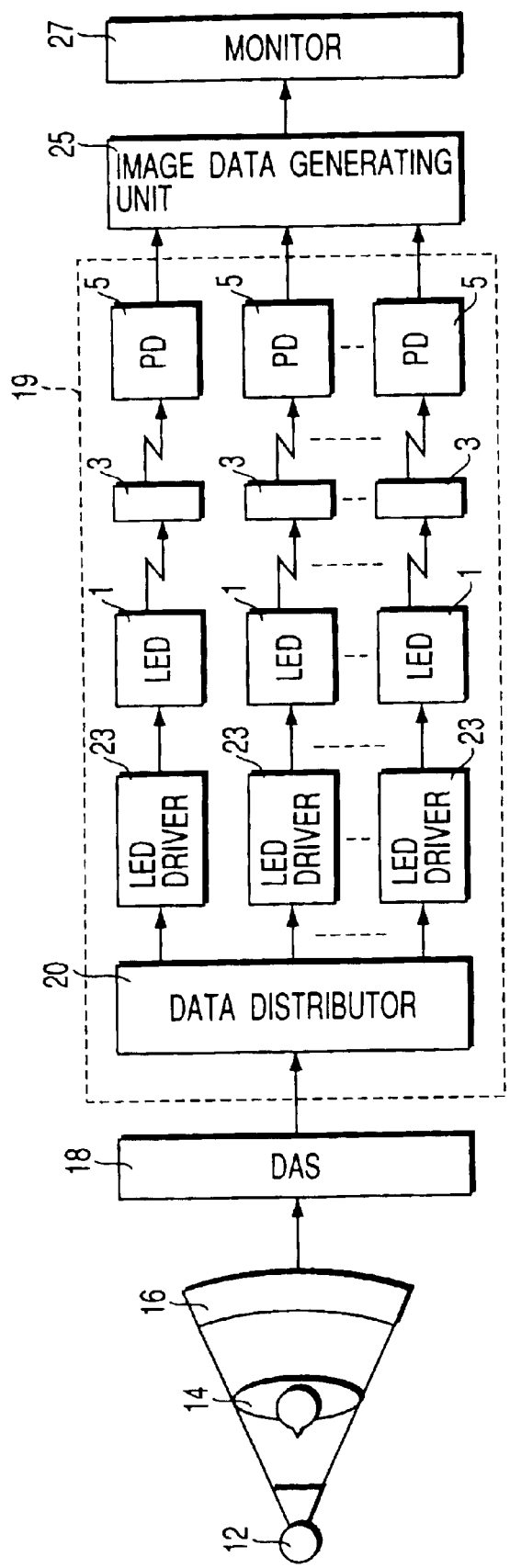
FIG. 5 is a block diagram showing the arrangement of the noncontact type signal transmission device in FIG. 1, together with the arrangement of the X-ray computed tomography apparatus.

FIG. 4 schematically shows the internal structure of the gantry of an X-ray computed tomography apparatus according to the first embodiment of the present invention. FIG. 5 is a block diagram showing the circuit arrangement of the X-ray computed tomography apparatus according to the first embodiment of the present invention. The same reference numerals as in FIG. 4 denote the same parts in FIG. 5.

A gantry 7 is the main structure of the X-ray computed tomography apparatus for acquiring multi-directional projection data about an object. The gantry 7 has a stationary portion 8 and ring-like rotating ring 10.

The rotating ring 10 is supported on the stationary portion 8 so that it can rotate about a rotation axis RA. A motor (not shown) is used to rotate the rotating ring 10 at a speed as high as less than one sec per rotation. With this operation, the rotating ring 10 undergoes displacement relative to the stationary portion 8.

An X-ray tube 12 for generating X-rays in the form of a fan is mounted on the rotating ring 10. In addition, an X-ray detector 16 is mounted on the rotating ring 10 to detect X-rays that are generated by the X-ray tube 12 and transmitted through an object 14. Typically, the X-ray detector 16 complies with multichannel specifications. A DAS (Data Acquisition System) 18 is also mounted on the rotating ring 10. The DAS 18 amplifies a weak electrical signal output from the X-ray detector 16 and converts the amplified electrical signal into a binary (1 and 0) digital signal. Note that a signal output from the DAS 18 will be referred to as projection data.

This projection data is transmitted to the stationary portion 8 side through a noncontact type signal transmission device 19. An image data generating unit 25 reconstructs tomographic data about the object on the basis of the transmitted projection data. A monitor 27 visualizes the tomographic data.

The noncontact type signal transmission device 19 is configured to perform noncontact transmission of projection data from the rotating ring 10 side to the stationary portion 8 side by using light. For this purpose, the noncontact type signal transmission device 19 includes a plurality of light-emitting diodes 1 and a plurality of light-receiving devices 5. Typically, the light-emitting diode 1 is a light-emitting diode, and the light-receiving device 5 is a photodiode.

Figure 6:
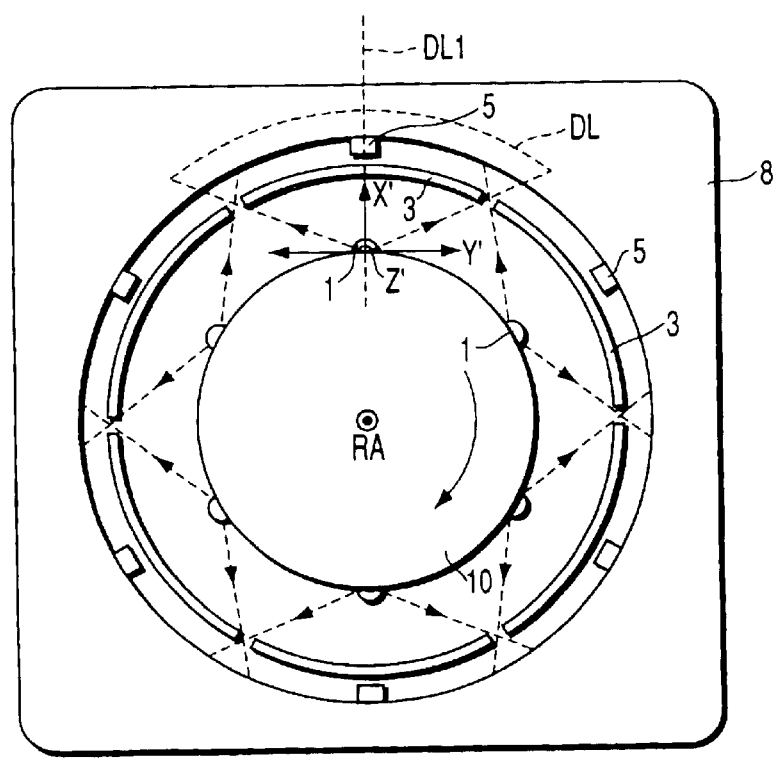
FIG. 6 is a view showing the structure of the noncontact type signal transmission device in FIG. 1.

As shown in FIG. 6, the light-emitting diodes 1 are arranged at predetermined intervals on the outer surface of the rotating ring 10. This interval is set such that the irradiation area from one light-emitting diode 1 overlaps that from another adjacent light-emitting diode 1. The photodiodes 5 are arranged at predetermined intervals on the inner surface of the ring of the stationary portion 8 to oppose the light-emitting diodes 1.

The noncontact type signal transmission device 19 also includes a plurality of LED drivers 23 for driving the light-emitting diodes 1 to simultaneously turn them on/off in accordance with projection data, and a data distributor 20 for distributing projection data to the LED drivers 23. The LED drivers 23 and data distributor 20 are mounted on the rotating ring 10. Each LED driver 23 turns on the light-emitting diode 1 when, for example, projection data is "1", and turns it off when the projection data is "0". The light emitted from the light-emitting diode 1 is incident on the photodiode 5. The photodiode 5 detects the incident light and generates an electrical signal having an amplitude corresponding to the amount of light received. The noncontact type signal transmission device 19 further includes a circuit (not shown) for binarizing the electrical signal output from the photodiode 5 and reconstructing the projection data. This reconstruction circuit is mounted on the stationary portion 8.

The noncontact type signal transmission device 19 also has a plurality of beam condensing devices 3. The beam condensing devices 3 are respectively provided for the pairs of light-emitting diodes 1 and photodiodes 5. The beam condensing devices 3 are cylindrical lenses, Fresnel lenses, or curved mirrors, typically cylindrical lenses each having a shape concentrically curved with respect to the rotating ring 10.

Figure 7:
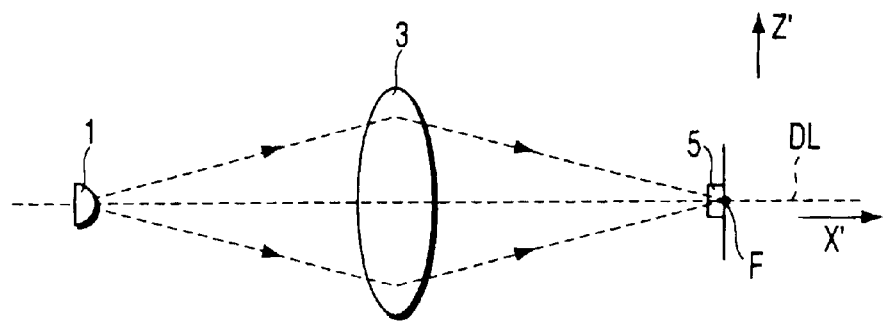
FIG. 7 is a view showing a light beam condensed by a beam condensing device.

FIG. 7 shows the optical mechanism of the cylindrical lens 3. The cylindrical lens 3 has the function of condensing light from the light-emitting diode 1 in a direction (Z'-axis) substantially perpendicular to the rotational orbit (Y'-axis). The cylindrical lens 3 does not have a function of condensing light from the light-emitting diode 1 or it has the function of diffusing light in a direction substantially parallel to the rotational orbit (Y'-axis).

When the light sent onto the lens 3 is viewed from the rotation axis direction of the ring 10, the light from the light-emitting diode 1 diverges in the form of a fan. This light also diverges in the form of a fan after passing through the lens 3. That is, when the traveling direction of light from the light-emitting diode is considered with respect to the Y' direction and Z' direction, respectively, the traveling direction of light from the light-emitting diode 1 does not change with respect to the Y' direction regardless of the lens 3. With respect to the Z' direction, however, the traveling direction of light from the light-emitting diode 1 changes in the direction in which the light is condensed by the lens 3. Therefore, the light from the light-emitting diode 1 is not condensed to one point but is condensed in a linear or belt-like form along the orbit of the photodiode 5.

The condensing function of the cylindrical lens 3 makes it possible to ensure a relatively large light reception amount even if the photodiode 5 is located relatively far from the light-emitting diode 1. With the cylindrical lens 3, therefore, even light that does not strike the effective light-receiving surface of the photodiode 5 without the cylindrical lens 3 can be sent onto the effective light-receiving surface of the photodiode 5.

The positional relationship between the light-emitting diode 1, the cylindrical lens 3, and the photodiode 5 is set as follows.

Figure 8A:
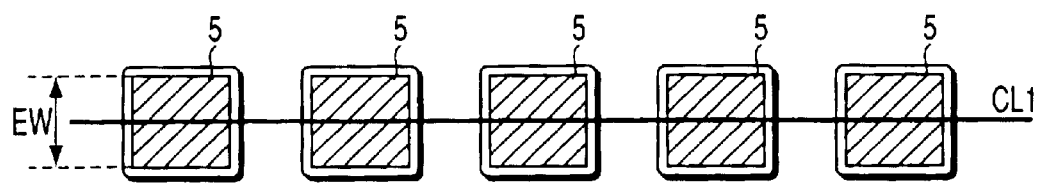
FIG. 8A is a view showing an irradiation area in which a light beam is condensed in the form of a line by the beam condensing device in FIG. 6.

For example, as shown in FIGS. 7 and 8A, the positional relationship between these three components is set such that the photodiode 5 is irradiated with light from the light-emitting diode 1 within an area CL1 having a width smaller than the effective light-receiving surface (EW) of the photodiode 5. In this case, the photodiode 5 is positioned at or close to a point F to which light is condensed by the cylindrical lens 3. With this positioning, almost all light is received by the photodiode 5 in the Z'-axis direction. Therefore, the amount of light received increases.

Figure 8B:
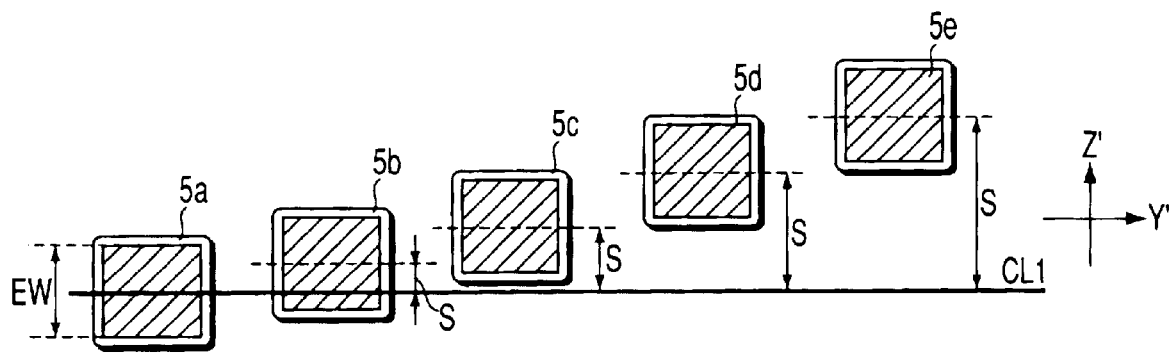
FIG. 8B is a view showing an irradiation area in which a light beam is condensed in the form of a line by the beam condensing device in FIG. 6.

As showing FIG. 8B, if some mechanical error (a mounting error and displacement in the rotational orbit in the Z' direction) or some photodiode position variation in the Z' direction (in this case, photodiode 5 are mounted in a inclined line to the light emitting diode line) occurs, the irradiation area CL1 may fall outside the effective light-receiving surface of the photodiode 5 and may receive no light. For example, in FIG. 8B, photodiode 5c can't receive light, in this case, the communication is broken. The positional relationship between the three components which is set to solve this problem will be described next.

Figure 9:
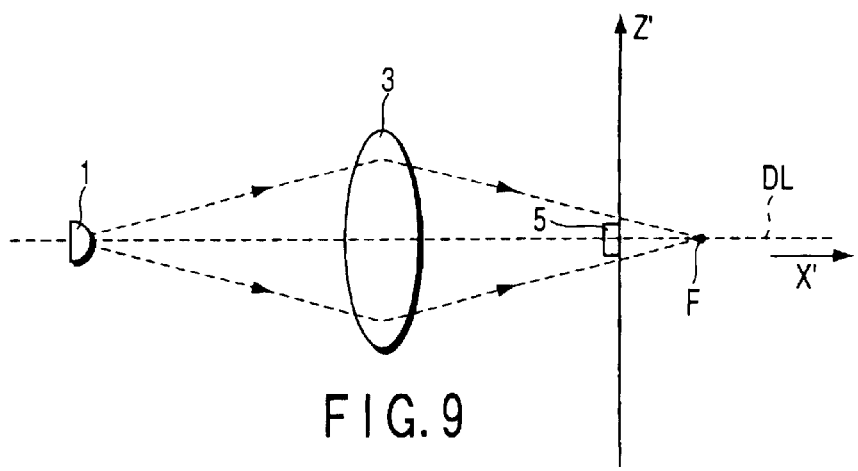
FIG. 9 is a view showing other light beam condensed by the beam condensing device in the first embodiment.
Figure 10:
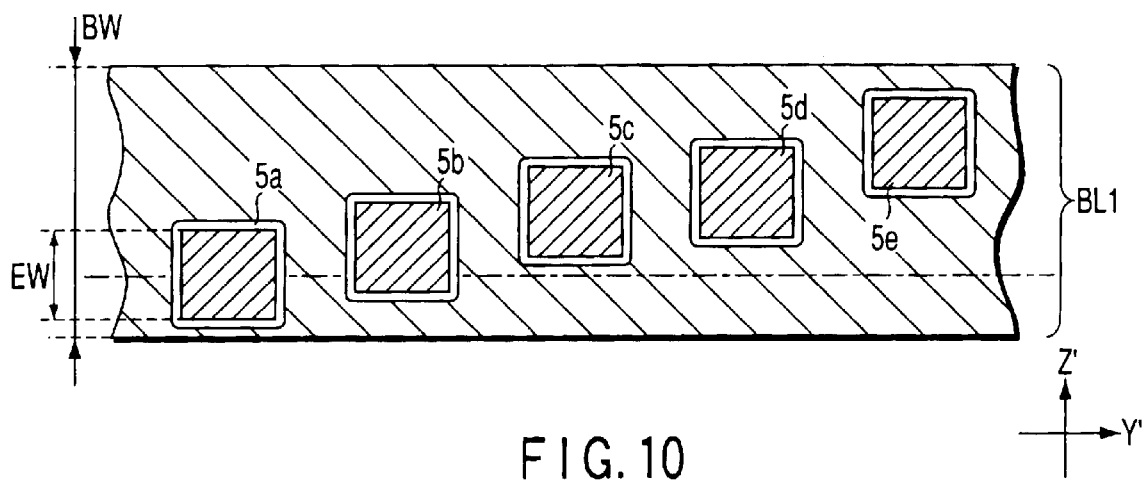
FIG. 10 is a view showing an irradiation area in which a light-beam is condensed in a belt form in the first embodiment.

As shown in FIGS. 9 and 10, the positional relationship between the three components is set such that the photodiode 5 is irradiated with light from the light-emitting diode 1 within a belt-like area BL1 having a width BW substantially equal to or larger than the width EW of the effective light-receiving surface of the photodiode 5. In this case, the point F is positioned farther from the light-emitting diode 1 than the photodiode 5. The positional relationship between the three components is set such that the width of the belt-like irradiation area BL1 becomes larger than, for example, the width of the effective light-receiving surface of the photodiode 5 by a mechanical error (a mounting error or displacement in the rotational orbit in the Z' direction) or a photodiode position variation in the Z' direction. In this case, the cylindrical lens 3 is preferably mounted on the ring of the stationary portion 8.

With this positional relationship, allowance with respect to a mechanical error such as a mounting error or rotation displacement or a photodiode position variation in the Z' direction increases as compared with the case shown in FIG. 7. In FIG. 7, photodiodes 5a, 5b can receive light, in FIG. 10, photodiodes 5a, 5b, 5c, 5d and 5e can receive light.

Figure 11:
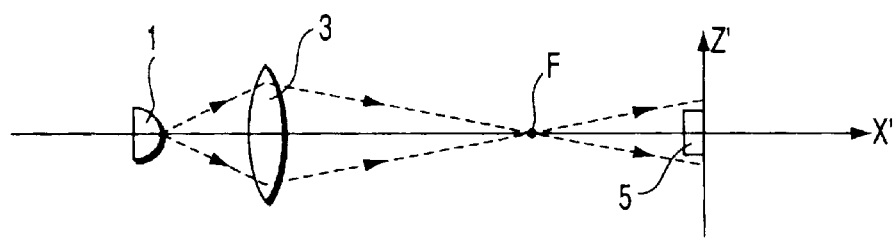
FIG. 11 is a view showing further other light beam condensed by the beam condensing device in the first embodiment.
Figure 12:
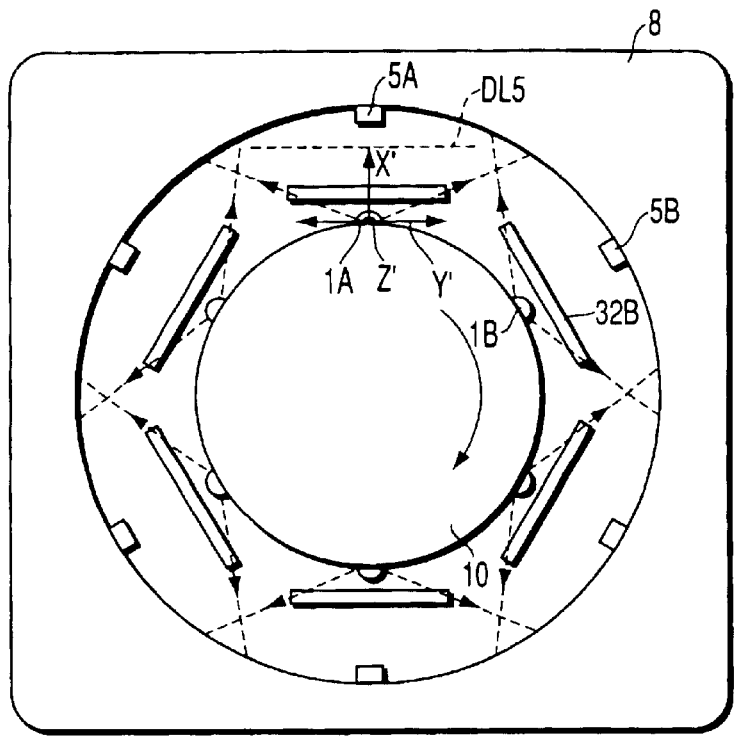
FIG. 12 is a view showing the structure of the noncontact type signal transmission device, which corresponds to FIG. 11.

As shown in FIG. 11, the positional relationship between the three components may be set such that the photodiode 5 is irradiated with light within the above belt-like area BL1. In this case, the point F is positioned between the lens 3 and the photodiode 5. With this positional relationship, a certain amount of light received can be ensured even with some mechanical error such as a mounting error or rotation displacement or a photodiode position variation in the Z' direction. In this case, the cylindrical lens 3 is preferably mounted on the rotating ring 10.

As described above, according to this embodiment, the light reception amount can be increased (the occurrence ratio of transmission errors can be decreased) within the allowable ranges of photodiode position variation in the Z' direction and rotation offsets of the rotating ring 10. That is, a reduction in the amount of light received by each photodiode 5 can be suppressed by substantially condensing light emitted from the light-emitting diode 1 onto the orbit of the photodiode 5, even if the amount of light emitted from the light-emitting diode 1 decreases. Even if, therefore, the amount of light emitted from the light-emitting diode 1 decreases due to an increase in the frequency of a transmission signal, an increase in communication error ratio can be suppressed.

In addition, since light from the light-emitting diode 1 is not condensed to one point on the orbit but is condensed to the entire orbit, each photodiode 5 can always receive light while moving on the orbit. This makes it possible to continuously transmit signals with small numbers of light-emitting diodes 1 and photodiodes 5.

Second Embodiment

Figure 13:
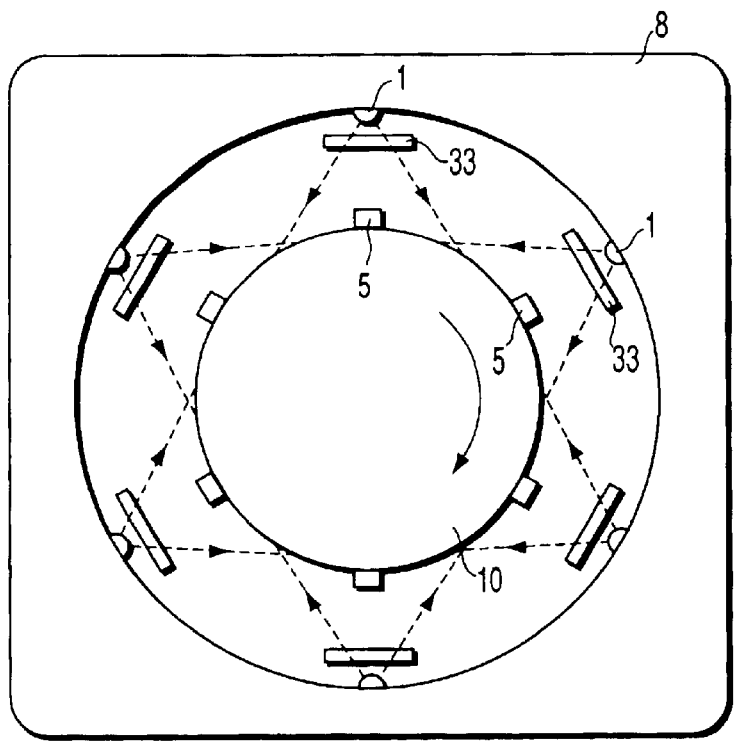
FIG. 13 is a view showing the structure of a noncontact type signal transmission device according to the second embodiment of the present invention.

FIG. 13 shows the arrangement of a noncontact type signal transmission device according to the second embodiment of the present invention. The same reference numerals as in FIG. 6 denote the same parts in FIG. 13.

In the first embodiment, the light-emitting diodes 1 are arranged on the rotating ring 10, and the photodiodes 5 are arranged on the stationary portion 8. In the second embodiment, light-emitting diodes 1 are mounted on a rotating ring 10, and photodiodes 5 are mounted on a stationary portion 8. Fresnel lenses 33 are used as beam condensing devices. The Fresnel lenses 33 are mounted on the stationary portion 8, together with the light-emitting diodes 1.

FIG. 14A is a sectional view of the Fresnel lens 33 used in this embodiment. FIG. 14B is a front view of this lens. A general Fresnel lens is made up of a plurality of annular lenses. In this embodiment, however, each Fresnel lens 33 is made up of a plurality of belt-like lenses each having a linear shape instead of an annular shape.

As shown in FIG. 14A, each Fresnel lens 33 has a sawtooth-like cross-sectional shape (the oblique portions of the respective teeth are not linear but have the same curvature). In addition, as shown in FIG. 14B, when viewed from the front side of each Fresnel lens, strips each having a predetermined width are arranged parallel.

This Fresnel lens 33 is thinner than the cylindrical lens 3 in the first embodiment and has a similar beam condensing function. With the Fresnel lenses, therefore, the same effects as those of the first embodiment can be obtained.

In addition, since the Fresnel lenses are thinner than the lenses in the first embodiment, a reduction in weight and improvement in heat dissipation characteristics can be attained.

As shown in FIG. 15, the Fresnel lenses 33 may be mounted on the rotating ring 10, together with the photodiodes 5.

Third Embodiment

As beam condensing means, curved mirrors, e.g., elliptic mirrors, are used instead of lenses. The elliptic mirrors are not disposed between light-emitting diodes and photodiodes but are disposed behind the light-emitting diodes or photodiodes.

Figure 16:
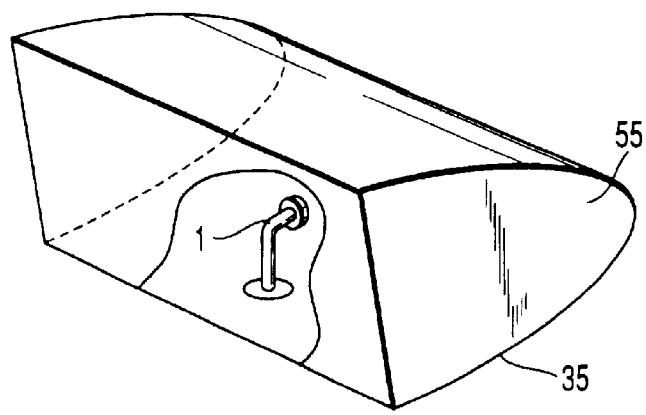
FIG. 16 is a view showing a beam condensing reflecting mirror mounted in a noncontact type signal transmission device according to the third embodiment of the present invention.

FIG. 16 is a perspective view showing the shape of an elliptic mirror and the position of a light-emitting diode. A light-emitting diode 1 is disposed in an elliptic mirror 35 and emits light toward the mirror surface of the elliptic mirror 35. A shielding plate 55 is disposed to be perpendicular to the generatrix of the elliptic mirror 35.

Figure 17:
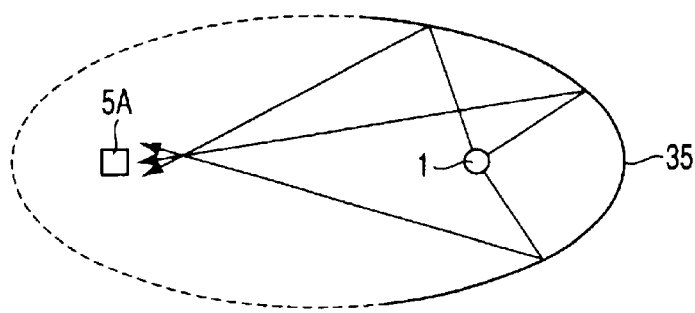
FIG. 17 is a view showing the positions of a light-emitting diode and photodiode with respect to the reflecting mirror.

FIG. 17 shows the positions of the light-emitting diode 1 and a photodiode 5 with respect to the elliptic mirror 35. The light-emitting diode 1 is positioned at one focal point of the elliptic mirror 35, and the photodiode 5 is disposed at a position slightly farther from the light-emitting diode 1 than the other focal point of the elliptic mirror 35. Light emitted from the light-emitting diode 1 is reflected by the elliptic mirror 35 and condensed to the other focal point. The reflected light converges first to the focal point and then diverges to reach the photodiode 5.

Figure 18:
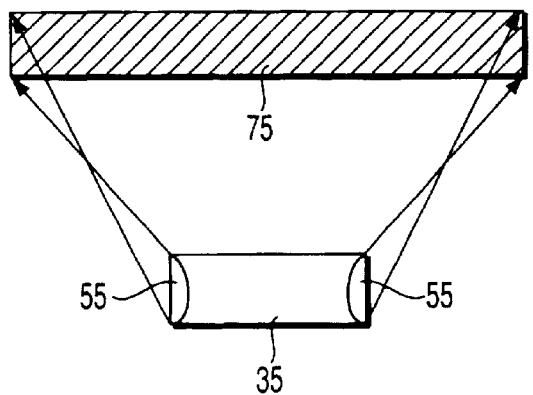
FIG. 18 is a view showing an irradiation area in which a light beam is condensed by the reflecting mirror in FIG. 16.

FIG. 18 shows the light condensed to the belt-like irradiation area when viewed from the rear side of the elliptic mirror. In this embodiment using the elliptic mirrors 35, light emitted from each light-emitting diode 1 is condensed onto one line before the orbit of the photodiode 5, and then diverges to be condensed, as light having a belt-like irradiation area 75, onto the orbit of the photodiode 5 as in the first embodiment using the cylindrical lenses. Note that the shielding plates 55 perpendicular to the generatrix of the elliptic mirror 35 are disposed on the right and left ends of the elliptic mirror 35 to suppress the diffusion of light in the generatrix direction, thereby preventing crosstalk.

Each elliptic mirror may be disposed behind the corresponding photodiode when viewed from the light-emitting diode. In this case, the light-emitting surfaces of the light-emitting diodes and the light-receiving surfaces of the photodiodes are located in the opposite directions to those in the third embodiment.

By substantially condensing light emitted from the light-emitting diode 1 onto the orbit of the photodiode 5 by using the elliptic mirror, the same effects as those of the first embodiment can be obtained.

The elliptic mirror is disposed behind the light-emitting diode when viewed from the photodiode, or behind the photodiode when viewed from the light-emitting diode. For this reason, the interval between the light-emitting diode and the photodiode can be reduced as compared with the first and second embodiments in which the lens is disposed between the light-emitting diode and the photodiode. This makes it possible to reduce the size of the apparatus.

In the use of elliptic mirrors, as in the first and second embodiments, the light-emitting diodes or photodiodes can be arranged on the rotating portion or stationary portion. In addition, the elliptic mirrors can be arranged on the rotating portion or stationary portion like the cylindrical lenses and Fresnel lenses used in the first and second embodiments. If light emitted from each light-emitting diode is substantially condensed onto the orbit of a corresponding photodiode, the same effects as those of the first embodiment can be obtained, regardless of the positions of light-emitting diodes, photodiodes, and elliptic mirrors.

In each embodiment described above, light emitted from a light-emitting means is substantially condensed onto the orbit of a light-receiving means by using one beam condensing means. However, the present invention is not limited these embodiments. Light may be condensed by using two or more beam condensing means.

For example, light emitted from a light-emitting means light may be collimated by the first beam condensing means, and this collimated beam is sent onto the second beam condensing means to make the second beam condensing means substantially condense the collimated beam onto the orbit of the light-receiving means.

The present invention can be applied to a case wherein both the light-emitting means and the light-receiving means move as well as a case wherein only one of the light-emitting means and the light-receiving means moves. The case in which both the light-emitting means and the light-receiving means move includes not only a case wherein the light-emitting means and light-receiving means move in different directions but also a case wherein they move in the same direction at different moving speeds. Furthermore, these means may move on a straight line or circumference.

Each light-emitting means may be formed by only an electrooptic conversion element for generating light modulated in accordance with a signal obtained by coding information to be transmitted or may be made up of a combination of an element that keeps emitting light regardless of the signal and an element for modulating the luminance or the like of the transmitted light in accordance with the signal. The electrooptic conversion element includes a laser diode in addition to a light-emitting diode. The element for modulating transmitted light includes a liquid crystal polarizing plate. Modulated light may be sent onto the light-receiving means through a medium that transmits light instead of being directly sent onto the light-receiving means. The medium for transmitting light includes an optical fiber.

The light-receiving means may be formed by only an element (optoelectric conversion element) for detecting the modulation of received light and converting the light into an electrical signal, or may be made up of an optoelectric conversion element and a medium for transmitting received light to the optoelectric conversion element. The optoelectric conversion element includes a phototransistor and photocell in addition to a photodiode.

The beam condensing means includes a curve mirror other than an aspherical lens and elliptic mirror as well as a cylindrical lens, Fresnel lens, and elliptic mirror.

The case wherein the position of the light-receiving means changes relative to the light-emitting means and beam condensing means includes a case wherein the moving directions and speeds of the light-emitting means and beam condensing means differ from those of the light-receiving means.

Likewise, the case wherein the position of the light-emitting means changes relative to the light-receiving means and beam condensing means includes a case wherein the moving directions and speeds of the light-receiving means and beam condensing means differ from those of the light-emitting means.

When the number of light-emitting means differs from that of light-receiving means, the beam condensing means are preferably disposed on the minority side. This arrangement requires a smaller number of beam condensing means, and hence makes it possible to facilitate design and manufacture and attain a reduction in cost and the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:

an X-ray tube for irradiating an object with X-rays;

a detector for detecting X-rays transmitted through the object;

a noncontact type signal transmission device for transmitting a signal output from said detector;

a unit for generating image data on the basis of the signal transmitted through said noncontact type signal transmission device; and a unit for displaying the image data, wherein said noncontact type signal transmission device comprises:

a stationary portion;

a rotating ring disposed inside said stationary portion;

a plurality of light-emitting devices discretely arranged on an outer surface of said rotating ring;

a plurality of light-receiving devices discretely arranged on an inner surface of said stationary portion; and a plurality of beam condensing devices arranged between said light-emitting devices and said light-receiving devices and having the function of condensing light in a direction parallel to a rotation axis of the rotating ring.

* * * * *